United States Patent
Dobree et al.

(10) Patent No.: US 12,209,061 B2
(45) Date of Patent: Jan. 28, 2025

(54) INTEGRATED PRODUCTION OF UREA FOR DIESEL EXHAUST FLUID AND UREA AMMONIUM NITRATE

(71) Applicant: STAMICARBON B.V., Sittard (NL)

(72) Inventors: Joey Dobree, Sittard (NL); Johannes Henricus Mennen, Sittard (NL)

(73) Assignee: STAMICARBON B.V., Sittard (NL)

(\*) Notice: Subject to any disclaimer, the term of this patent is extended or adjusted under 35 U.S.C. 154(b) by 0 days.

(21) Appl. No.: 17/368,924

(22) Filed: Jul. 7, 2021

(65) Prior Publication Data
US 2021/0331086 A1    Oct. 28, 2021

Related U.S. Application Data

(62) Division of application No. 15/560,460, filed as application No. PCT/NL2016/050213 on Mar. 29, 2016, now Pat. No. 11,083,976.

(30) Foreign Application Priority Data

Mar. 25, 2015 (EP) .................................. 15160826

(51) Int. Cl.
 C07C 273/04    (2006.01)
 B01D 3/00     (2006.01)
 (Continued)

(52) U.S. Cl.
 CPC .............. *C07C 273/04* (2013.01); *B01D 3/00* (2013.01); *B01D 3/009* (2013.01); *B01J 19/002* (2013.01); *C01C 1/185* (2013.01); *C05C 1/00* (2013.01); *C05C 9/00* (2013.01); *C05G 5/23* (2020.02); *C07C 273/02* (2013.01); (Continued)

(58) Field of Classification Search
 None
 See application file for complete search history.

(56) References Cited

U.S. PATENT DOCUMENTS

| 2,087,325 A | 7/1937 | Lawrence et al. |
| 3,691,729 A | 9/1972 | De Rooy |

(Continued)

FOREIGN PATENT DOCUMENTS

| EP | 1856038 | 11/2007 |
| EP | 2784062 | 10/2014 |

(Continued)

OTHER PUBLICATIONS

Chematur Engineering Group. Business Area Nitric Acid: UAN Solution. (Year: 2014).*

(Continued)

*Primary Examiner* — Jennifer A Leung
(74) *Attorney, Agent, or Firm* — Leason Ellis LLP

(57) ABSTRACT

Disclosed is a method for the integrated production of two different urea products. One is an aqueous urea solution suitable for use in NOx abatement (generally indicated as Diesel Exhaust Fluid DEF). The other is a solution used as a fertilizer, viz. Urea Ammonium Nitrate (UAN). The production of DEF and UAN are integrated as follows: ammonia recovered from the production of urea is used as a feed to the production of ammonium nitrate. At least part of an aqueous urea stream from urea production, is mixed with ammonium nitrate so as to obtain UAN.

4 Claims, 3 Drawing Sheets

(51) Int. Cl.
  *B01J 19/00*   (2006.01)
  *C01C 1/18*    (2006.01)
  *C05C 1/00*    (2006.01)
  *C05C 9/00*    (2006.01)
  *C05G 5/23*    (2020.01)
  *C07C 273/02*  (2006.01)
  *C07C 273/10*  (2006.01)
  *C07C 273/14*  (2006.01)
  *C07C 275/02*  (2006.01)

(52) U.S. Cl.
  CPC .......... *C07C 273/10* (2013.01); *C07C 275/02* (2013.01); *B01J 2219/00002* (2013.01); *B01J 2219/00024* (2013.01); *B01J 2219/00105* (2013.01); *Y02P 20/10* (2015.11)

(56) References Cited

U.S. PATENT DOCUMENTS

| | | |
|---|---|---|
| 4,115,449 A | 9/1978 | Biermans |
| 4,174,379 A | 11/1979 | Froehlich et al. |
| 2008/0118414 A1 | 5/2008 | Pagani |
| 2011/0124495 A1 | 5/2011 | Zardi |
| 2013/0207035 A1 | 8/2013 | Meessen |
| 2017/0260061 A1 | 9/2017 | Mennen |
| 2017/0283372 A1 | 10/2017 | Morikawa |

FOREIGN PATENT DOCUMENTS

| | | |
|---|---|---|
| WO | 20130055219 | 4/2013 |
| WO | 20160085343 | 6/2016 |

OTHER PUBLICATIONS

International Preliminary Report on Patentabilty for PCT/NL2016/050213, dated Jul. 13, 2017, 9 pages.
EMFA Publication , "Best Available Techniques for Pollution Prevention and Control in the European Fertilizer Industry Production of Urea and Urea Ammonium Nitrate 2000 EFMA European Fertilizer Manufacturers' Association", Jan. 1, 2000. 44 pages.
Thyssenkrupp Uhde Wins Major US Projects, Andy Brice, ICIS Chemical Business; Apr. 15-Apr. 21, 2013; 283, 13; ProQuest p. 32. (Year: 2013).
Meessen, "Urea" in: Ullmann's Encyclopedia of Industrial Chemistry, Wiley-VCH Verlag GmbH & Co. KGaA, Weinheim, Germany (2010) 39 pages.
International Search Report and Written Opinion for PCT/NL2016/050213, mailed Aug. 10, 2016, 11 pages.

\* cited by examiner

INTEGRATED PRODUCTION OF UREA FOR DIESEL EXHAUST FLUID AND UREA AMMONIUM NITRATE

CROSS-REFERENCE TO RELATED PATENT APPLICATIONS

This application is a divisional application of U.S. patent application Ser. No. 15/560,460 filed on Sep. 21, 2017, which was a U.S. National Stage Application under 35 U.S.C. § 371 of International Patent Application No. PCT/NL2016/050213, filed Mar. 29, 2016, which claims the benefit of priority of European Patent Application No. 1516026.2 filed Mar. 25, 2016, all of which are incorporated by reference in their entireties.

FIELD OF THE INVENTION

The invention is in the field of the production of urea, and in particular pertains to a method for the combined production of a urea solution suitable for the abatement of $NO_x$ in combustion engine exhaust gases, for example exhaust gases produced from Diesel engines (DEF: Diesel Exhaust Fluid), and the production of urea ammonia nitrate solution (UAN). The invention also pertains to a plant for carrying out the method.

BACKGROUND OF THE INVENTION

Urea is generally produced from ammonia and carbon dioxide. It can be prepared by introducing an ammonia excess together with carbon dioxide at a pressure between 12 and 40 MPa and at a temperature between 150° C. and 250° C. into a urea synthesis section. Typical urea production plants further comprise a recovery section and a finishing section. In the recovery section non-converted ammonia and carbon dioxide are recovered and recirculated to the synthesis section. The recovery section is generally followed by an evaporation section. Therein the urea concentration is further increased by the evaporation of water, resulting in a highly concentrated solution that is generally referred to as a urea melt. In the finishing section, typically, the urea melt is brought into a desired solid, particulate form, generally involving techniques such as prilling, granulation, or pelletizing.

In the evaporation section still considerable amounts of CO2 and particularly NH3 are removed. By treatment in a scrubber the ammonia is removed. This then goes to a waste water treatment unit which is a very costly and energy intensive operation.

An interesting urea product is a solution for NOx abatement such as used in selective reduction, which may be a non-catalytic thermal process or a selective catalytic reduction (SCR) process. An example of a solution for SCR is diesel exhaust fluid (DEF), which term is used in description to generally refer to urea solutions for NOx abatement.

DEF is a 32.5 wt. % urea solution in demineralized water with a composition that has maximum 0.3 wt. % biuret and maximum 0.2 wt. % of alkalinity as ammonia. DEF is marketed under the (commercial) trade names Ad-Blue*, Air1®, Arla 32 and AUS-32 and is injected in the tail gas of combustion engines to capture $NO_x$ to prevent it from escaping to the atmosphere. The purpose of the DEF is to convert the $NO_x$ via the reaction: urea+$NO_x$→$N_2$+$H_2O$ into harmless nitrogen and water. Reduction of $NO_x$ from combustion engines is widely applied as $NO_x$ is one of the main sources for environmental pollution indicated for global warming such as the Global Warming Potential (GWP), Tropospheric Ozone Formation Potential (TOFP) and Ozone Depletion Potential (ODP).

The production of Diesel Exhaust Fluid (DEF) is generally achieved by dissolving solid urea product in demineralized water. The solid urea product, for example produced via one of the aforementioned finishing technologies and the demineralized water are combined and the solution is mixed until the urea is fully dissolved. This method has the disadvantage that significant investment is needed in urea finishing technology and also that by-products such as additives used or produced during finishing, for example formaldehyde or biuret (which is a urea byproduct), need to be removed to produce a product of the desired specification. Typical biuret concentrations in finished products are 0.9 to 1.1 wt. %. This consequently results in a biuret content in final DEF product which is over 0.3 wt. % thus resulting in off spec material. The current specification according to ISO 22241 allows maximum 0.3%. The higher biuret concentration results in a less effective DEF solution with respect to the capture of $NO_x$ as less urea is available to capture the $NO_x$. Furthermore, during the production of granulate and prills large amounts of water are removed which are later added during the dissolution step. This requires significant amounts of energy which leads to additional costs.

An improved process, disclosed in EP1856038A1, is to use a urea aqueous solution obtained directly from or after the recovery section of the urea melt plant, and dilute said urea aqueous solution with water to obtain the desired solution. The urea aqueous solution would otherwise be sent to the evaporation section to remove the water from the urea melt for the production of solid urea via fluid bed granulation, pelletizing or prilling. In this way the need for evaporation of water is eliminated, but the urea aqueous solution may contain relatively high levels of ammonia which exceed the specification for the final DEF product. EP1856038A1 discloses that the ammonia level (as free ammonia or in the form of ammonium carbamate) in the solution may be reduced by subjecting the urea aqueous solution to dissociation, for example by the addition of heat or the reduction of pressure, optionally with the addition of a stripping medium or a combination of the foregoing. This step is effectively the same as and may be carried out in the same type of equipment as the evaporation step in a conventional finishing section of a urea plant and is therefore sometimes called 'evaporation step' or 'pre-evaporation step'. The pre-evaporation step is designed to produce a urea aqueous solution which, after dilution with water, meets the requirements of Diesel Exhaust Fluid.

A major disadvantage is that the pre-evaporating step releases ammonia with inerts from the urea aqueous solution which may need to be removed to meet ammonia emission regulations, requiring a dedicated condensation/scrubbing section and a subsequent waste water treatment section integrated with the urea melt plant in order to recover the ammonia released.

Urea Ammonium Nitrate (UAN) is a fertilizer which is generally used as an aqueous solution of urea and ammonium nitrate. Ammonium nitrate is produced by reacting ammonia with a strong solution of nitric acid while maintaining the pH of the solution within narrow boundaries. The resulting solution is then mixed with an aqueous urea solution to obtain UAN. Typical UAN products contain 28 wt. % to 32 wt. % of total nitrogen and typically of from 29 wt. % to 38 wt. % urea and of from 36 wt. % to 48 wt. % of ammonium nitrate, with the remainder being water.

The demand for UAN is generally subject to strong seasonal fluctuations, which makes it desirable to find a way to operate a plant for UAN in such a way that it can also be put to economically attractive use at times of low demands for UAN. It is thereby noted that an aqueous urea solution produced in a typical UAN plant for the production of a final UAN product cannot generally be used for the production of DEF. The ammonia concentration in the urea aqueous solution is generally higher (>2000 ppm wt.) than allowed in the production of DEF (<0.2 wt. %). Also, as the UAN product is a liquid, it is inconvenient and costly to transport over large distances.

It would be desired to combine the production of urea and UAN in such a way as to be able to compensate for low demands of UAN. It would be particularly desirable to provide such an arrangement for the combined production of urea and UAN, that a urea aqueous solution is obtained that meets the requirements for use as DEF. Further, it would be desired to provide a more economical way of dealing with ammonia waste from the urea evaporation section.

As a remote technical background, reference is made to U.S. Pat. No. 4,174,379. Herein a process is disclosed for the production of urea and UAN. The urea is produced by a once-through type urea production process. This type of urea production process is outdated, and has essentially different attributes than modern processes, which are almost exclusively stripping processes. E.g., whilst once-through processes by nature produce a low biuret content, biuret is an inevitable by-product from stripping a urea reaction solution. This is believed to be caused by the relatively high temperatures and concentrations prevailing in a urea stripper. As mentioned above, for DEF the presence of biuret can be tolerated only at very low levels (particularly as specified in the applicable ISO and DIN norms). Thus, the production of a urea solution suitable for being converted into DEF, is particularly challenging in the event that the urea is produced in a stripping process.

SUMMARY OF THE INVENTION

In order to better address one or more of the foregoing desires, the invention, in one aspect provides a process for the production of urea ammonium nitrate, comprising the steps of
  reacting nitric acid and ammonia in an ammonium nitrate production unit under conditions so as to obtain an aqueous ammonium nitrate solution;
  reacting carbon dioxide and ammonia under urea-forming conditions so as to obtain a reaction solution comprising water, urea, ammonium carbamate, and unreacted $CO_2$ and $NH_3$;
  subjecting said reaction solution to stripping so as to obtain unreacted ammonia and carbon dioxide, and a stripped reaction solution;
  recirculating said retrieved ammonia and carbon dioxide as starting materials for forming urea;
  subjecting said stripped reaction solution to separation so as to obtain an aqueous urea stream, and a gas stream comprising $CO_2$ and $NH_3$;
  feeding $NH_3$ from said gas stream as a reactant to said ammonium nitrate production unit;
  mixing at least part of said aqueous urea stream with said aqueous ammonium nitrate solution so as to obtain a urea ammonium nitrate solution.

In another aspect, the invention presents an integrated system for the production of urea and urea ammonium nitrate, said system comprising (i) a unit for the production of urea, said unit comprising a urea synthesis section comprising a reactor, a stripper and a condenser in fluid communication with each other so as to form a urea synthesis loop, and, downstream of the synthesis section and in fluid communication therewith, a urea purification section suitable for separating off $CO_2$ and $NH_3$ from an aqueous urea solution comprising said $CO_2$ and $NH_3$, and (ii) a unit for the production of ammonium nitrate from ammonia and nitric acid; wherein an outlet for $NH_3$ from the purification section of the urea plant is connected to an inlet for $NH_3$ of the unit for the production of ammonium nitrate, and wherein an outlet for an aqueous urea solution from the purification section and an outlet for an aqueous ammonium nitrate solution from the unit for the production of ammonium nitrate, are connected to a unit for mixing said aqueous urea solution and said aqueous ammonium nitrate solution.

In a further aspect, the invention is a method for the modernization of a urea plant comprising a urea synthesis section comprising a reactor, a stripper and a condenser in fluid communication with each other so as to form a urea synthesis loop, and, downstream of the synthesis section and in fluid communication therewith, a urea purification section suitable for separating off $CO_2$ and $NH_3$ from an aqueous urea solution comprising said $CO_2$ and $NH_3$, the method comprising adding to the urea plant a unit for the production of ammonium nitrate from ammonia and nitric acid, wherein an outlet for $NH_3$ from the purification section of the urea plant is connected to an inlet for $NH_3$ of the unit for the production of ammonium nitrate, and wherein an outlet for an aqueous urea solution from the purification section and an outlet for an aqueous ammonium nitrate solution from the unit for the production of ammonium nitrate, are connected to a unit for mixing said aqueous urea solution and said aqueous ammonium nitrate solution.

In a still further aspect, the invention provides a method for the modernization of a plant for the production of urea ammonium nitrate, said plant comprising a unit for the synthesis of ammonium nitrate from ammonia and nitric acid, the method comprising adding to the plant for the production of ammonium nitrate a plant for the production of urea, whereby the plants are integrated in the manner described in the previous paragraph.

DETAILED DESCRIPTION OF THE INVENTION

Figure 1:
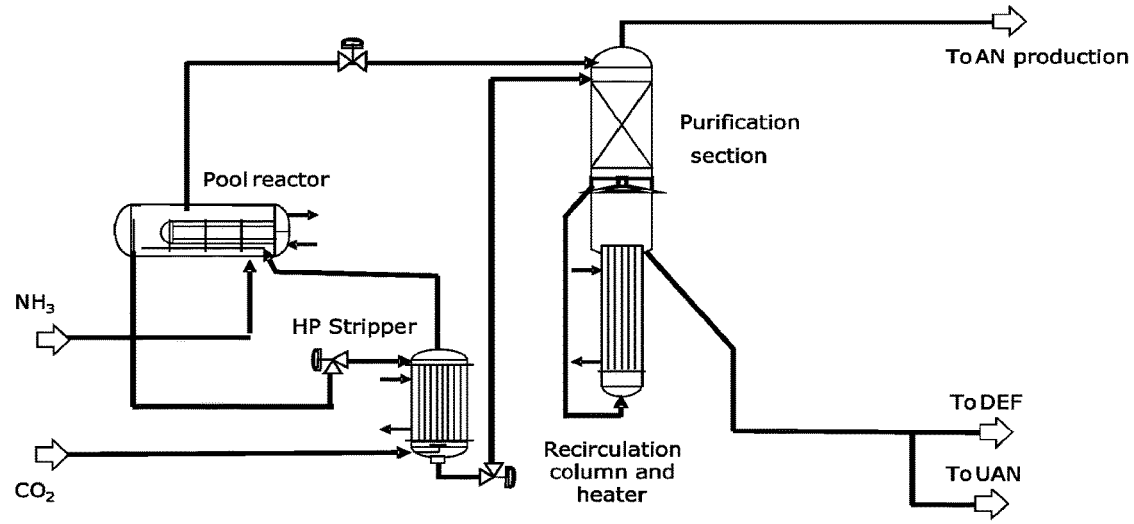
FIGS. 1 to 5 are all schematic drawings of equipment parts and process streams relating to embodiments of the invention

The invention is based on the judicious insight to integrate the production of DEF with the production of liquid UAN fertilizer. This provides a process which is economically attractive, flexible to meet market demands, as well as environmentally and energy friendly due to the low number of equipment, zero emissions and the possibility to eliminate the waste water treatment section. In accordance with the invention, the ammonia off-gas from urea production is sent to the AN section of a UAN plant, were the ammonia off-gasses (which can be both liquid ammonia or (possibly diluted) gaseous ammonia), are neutralized with nitric acid so as to form AN, and accordingly blended to UAN. So the off-gasses are not sent to an outside environment, but remain in the process.

Particularly, when integrating the DEF production with the production of UAN liquid fertilizer, a surprisingly low biuret concentration between 0.01 wt. % and 0.3 wt. % can be realized, even though the process involves producing urea by means of a stripping process. This low biuret content is believed to be achieved, inter alia, by the possibility to have a relatively small low Pressure (LP) recirculation section. Typically the LP recirculation (recovery) section of a urea stripping plant comprises a plurality of pieces of equipment, where in some areas high temperatures (such as around 135° C.) are applied. The biuret content is prone to increase due to a longer residence time in this LP section. The possibility of eliminating equipment can be advantageous in reducing the residence time in the LP section (e.g. limited to a single rectifying column). This, in turn, provides the benefit of a possibly reduced biuret formation.

In addition, in the process of the invention the vapor from the recovery section is sent to the ammonium nitrate section. In the conventional process these vapors are condensed to form carbamate solution and subsequently returned to the HP synthesis section. This leads effectively to a recycle of water to the synthesis section. In an interesting embodiment, the urea is produced in equipment set up specifically for producing DEF in conjunction with UAN. Particularly, the urea is thereby produced using a submerged condenser/reactor (which is a urea reactor integrated with a submerged carbamate condenser), for example a pool reactor which is a horizontal submerged condenser/reactor. In this configuration no water/carbamate needs to be recycled to the urea synthesis. This is advantageous, as it makes the urea synthesis more efficient.

Further, as the invention allows producing a urea solution dedicated for DEF, various process settings can be adapted so as to minimize biuret production. E.g., by lowering the temperature in the stripper. This can have a considerable effect, since biuret is predominately formed in the outlet thereof. It is also conceivable to reduce the temperature and increase the pressure in the LP section, to lower the ammonia content and biuret formation.

A result is that more urea is available in the DEF solution for NOx capture, resulting in a higher efficiency of the DEF final product in the application of thermal DeNOx. As a result the efficiency of Selective Non Catalytic Reaction (SNCR) technologies can be increased up to 20%. With this approach less urea will be converted in biuret, meaning that also more DEF final product can be produced based on the invention compared to existing solution, while approximately 1% less raw material is required per ton of DEF final product. In addition significant capital investment can be eliminated as no pre-evaporation, condensation and waste water treatment is required anymore. This can be achieved by using a pressurized urea solution directly from the recovery section.

The urea production process applied in the invention, results in an aqueous stream. Rather than evaporating said stream, with the need for waste water treatment, the method of the invention provides for flexibly putting it to use. At least part of the stream is used in the production of UAN, by combining it with ammonium nitrate. At the same time, ammonia obtained from the separation step that results in said aqueous urea stream, is used in the production of ammonium nitrate.

Preferably, the amount of the aqueous urea stream used in the production of UAN is at least an amount corresponding to the amount of ammonium nitrate produced from the amount of ammonia separated off from the urea production. This can be understood with reference to the fact that the urea ammonium nitrate solution comprises 29 wt. % to 38 wt. % of urea and 36 wt. % to 46 wt. % of ammonium nitrate. Thus, preferably, the part of the aqueous urea stream mixed with the ammonium nitrate solution is in an amount at least sufficient to provide the desired amount of ammonium nitrate obtainable by the amount of NH3 fed to the ammonium production unit.

According to the invention, a choice is given for the further use of the aqueous urea stream. This can either be used for obtaining DEF, or a further part (up to all) thereof can be used in the production of UAN. It will be understood that if more urea is applied to the production of UAN, also a corresponding higher amount of ammonium nitrate is to be provided. This can be ammonium nitrate from an external source, it can be ammonium nitrate produced in situ from ammonia and nitric acid, or both.

In the method of the invention, the UAN is produced by mixing aqueous urea with said aqueous ammonium nitrate so as to obtain a urea ammonium nitrate solution. The ammonium nitrate is produced by reacting ammonia and nitric acid.

The industrial production of ammonium nitrate entails the acid-base reaction of ammonia with nitric acid.

$$HNO_3 + NH_3 \rightarrow NH_4NO_3$$

Ammonia is normally used in its anhydrous form gas and the nitric acid is concentrated (typical concentration range: 40 to 80 wt. %, such as about 60 wt. %). Via an exothermic reaction, the ammonium nitrate solution is readily formed, typically at a concentration of about 70% to 95%, such as 83% to 88%. Whilst in making solid ammonium nitrate products, such as prills or granules, the excess water is evaporated to an ammonium nitrate (AN) content of 95% to 99.9% concentration, this step can be dispensed with when making a urea ammonium nitrate solution. This UAN solution can be made by mixing an aqueous urea solution with the ammonium nitrate solution.

The nitric acid used in the production of ammonium nitrate can be obtained as an external feed. Preferably, the nitric acid is produced on site, as this is generally more attractive from an economical point of view than relying on transportation of nitric acid.

Preferably, the method of the invention is conducted in an integrated system for the production of urea and urea ammonium nitrate. This system comprises (i) a unit for the production of urea and (ii) a unit for the production of ammonium nitrate from ammonia and nitric acid. The unit for the production of urea comprises a urea synthesis section of the stripping type and, downstream thereof and in fluid communication therewith, a urea purification section suitable for separating off CO2 and NH3 from an aqueous urea solution comprising said CO2 and NH3. According to the invention, an outlet for NH3 from the purification section of the urea production unit is connected to an inlet for NH3 of the unit for the production of ammonium nitrate, i.e. so as to provide NH3 separated off from urea production as a feed to the production of ammonium nitrate. Further, a provision is made for the aqueous urea stream obtained from the urea production unit to be mixed with the liquid ammonium nitrate obtained from the ammonium nitrate production unit. To this end, an outlet for an aqueous urea solution from the purification section of the urea production unit and an outlet for an aqueous ammonium nitrate solution from the unit for the production of ammonium nitrate, are connected to a unit for mixing said aqueous urea solution and said aqueous ammonium nitrate solution.

The invention also pertains to such an integrated system for the production of urea and urea ammonium nitrate. The system of the invention may or may not also include a unit for the production of nitric acid. The main industrial method to produce nitric acid is from ammonia.

Accordingly, anhydrous ammonia is oxidized to nitric oxide, in the presence of platinum or rhodium gauze catalyst at a high temperature of about 500 K and a pressure of 9 bar.

$$4NH_3\ (g) + 5O_2\ (g) \rightarrow 4NO\ (g) + 6H_2O\ (g)$$

Nitric oxide is then reacted with oxygen in air to form nitrogen dioxide.

$$2NO\ (g) + O_2\ (g) \rightarrow 2NO_2\ (g)\ (\Delta H = -114\ kJ/mol)$$

This is subsequently absorbed in water to form nitric acid and nitric oxide.

$$3NO_2\ (g) + H_2O\ (l) \rightarrow 2HNO_3\ (aq) + NO\ (g)\ (\Delta H = -117\ kJ/mol)$$

The nitrous oxide is cycled back for reoxidation. Alternatively, the last step can be carried out in air:

$$4NO_2\ (g) + O_2\ (g) + 2H_2O\ (l) \rightarrow 4HNO_3\ (aq)$$

The aqueous HNO3 obtained can be concentrated by distillation, generally up to about 68% by mass.

An advantage in respect of the method and system of the present invention, is that the nitric acid can be produced on a site that has an infrastructure for ammonia, as this is also used as a feed in the urea production.

In the event that the system of the invention comprises a unit for the production of nitric acid, this unit will generally be fed from external sources, and will have an outlet for nitric acid that is in fluid communication with an inlet for nitric acid of the unit for the production of ammonium nitrate.

The urea production unit can be a conventional urea stripping plant, fully equipped with, downstream of the synthesis and recovery sections, also an evaporation section, a waste water treatment section, and a finishing section. As an important benefit of the invention, however, it is possible to produce the urea for DEF and for UAN in a urea stripping production unit without an evaporation section and a wastewater treatment section. Also, the regular finishing section (serving to form solid urea forms such as granules, pellets or prills) can be dispensed with. For, in the process of the invention, DEF can be produced by diluting a part of the aqueous urea stream, obtained from separation of the urea reaction solution, with demineralized water. This results in a solution suitable for use in a unit for the reduction of NOx.

The method of the invention can also be conducted so as to produce DEF in a solid form. To this end, a part of the aqueous urea stream, obtained from separation of the urea reaction solution, can be subjected to flash crystallization. This serves to form a solid urea powder which is suitable to be converted by dilution with demineralized water into a solution suitable for use in a unit for the reduction of NOx. This is of great benefit, as it is much more economically attractive to transport a solid urea powder, rather than having to transport DEF as a solution, which would require transporting a great amount of water as of the DEF production site.

For the production of a solid urea product by flash crystallization, reference is hereby made to WO 2013/055219. The product disclosed therein is made by exerting a mechanical force on urea crystals. This step can be dispensed with for the production of powder that can be diluted to produce DEF. Particularly, a free flowing urea powder can be obtained by obtaining an aqueous urea stream as mentioned above, subjecting said stream to flash crystallization at subatmospheric pressure, so as to obtain a solid crystallized urea containing product and a vapor comprising water and ammonia, wherein the solid crystallized urea product contains less than 0.2 wt. % water; and preferably packaging the solid crystallized urea product under conditions such that the water content in the packaged product is maintained below 0.2 wt. %. Thereby the flash crystallization is preferably conducted at a pressure below 15 kPa, more preferably from 1 to 10 kPa. Further, the flashing is preferably conducted as dry flashing.

Flashing can be done in a flashing device, such as a dry flasher. A dry flasher is characterized in that a liquid stream is converted by crystallization and evaporation into substantially a solid and a vapor. In a dry flasher the process conditions are selected such that the amount of liquid remaining is substantially nil. This allows for a clean separation of the gas and the solids without substantial sticking and fouling. Another advantage of the dry flashing is that due to the absence of a slurry, no solid liquid separation such as a centrifuge, nor a re-melter is necessary. This allows a significantly simpler process scheme. Such a dry flasher is a vessel that operates preferably at a pressure in between 1 and 15 kPa and more preferably at a pressure in between 2 and 10 kPa. In said dry flasher the urea solution is distributed by a liquid distributer. By the expansion the urea and biuret crystallizes spontaneously in a solid and the remaining components comprising water, ammonia and small amounts of carbon dioxide evaporate.

The particle size of the obtained solid urea product by adiabatic flashing is in the range of from 0.1 μm to 1000 μm, preferably of from 1 μm to 800 μm.

In this embodiment, the process of the invention allows to produce a free flowing powder which can be packaged in bags (20 kg) or big bags (i.e., 500 kg or 1000 kg bags) which can be easily emptied on site to produce the DEF solution.

The urea powder produced by the process has a very low quantity of biuret, typically less than 0.5%, preferably less than 0.4% which translates into less than 0.20% or less than 0.15% wt. in the final DEF solution. This means that the amount of active urea in the solution will be consequently higher at the same solids content. The biuret specification for the final DEF solution is max 0.3% wt. When prills are used to prepare the solution, the biuret content in the solution is typically between 0.27 and 0.36% wt.

In this embodiment of the method of the invention, the solid crystallized urea product as obtained, is packaged under conditions such that the water content in the packaged product is maintained below 0.2 wt. %. This low moisture content serves to ensure that the solid urea, which is hygroscopic by nature, remains a powder that is capable of being released from its package, and reconstituted to a solution. According to the invention, the water content in the packaged product is maintained below the aforementioned level until the product is to be used for preparing a solution.

In practice this means that the powder obtained, which has the required low moisture content, is packaged in a non water-permeable package (e.g. a container or a bag). Suitable packaging materials include high density polyethylene. Other plastics suitable for packaging hygroscopic materials are known in the art. The packing material may be non-porous and sealed. Also, the package can consist of multi-layer material.

The aforementioned powder is intended to be used for obtaining DEF by dissolving it in demineralized water. It will be understood that it can also be used in making UAN, should such be desired, e.g. in the event of a high demand of UAN. In the latter case, the powder can be dissolved also in regular tap water.

In the process of the invention, the urea can synthesized by any suitable urea stripping process. Such processes are generally conducted in a stripping plant. The urea synthesis section of a stripping plant comprises at least one reactor, a stripper, and a condenser. These are generally operated at high pressure (HP), and in the art regularly referred to as a HP reactor, a HP stripper, and a HP carbamate condenser. The reactor, stripper, and condenser are in fluid communication with each other so as to form a urea synthesis loop. This does not require further elucidation to the skilled person. Generally, the reactor will produce an aqueous urea synthesis solution. Said solution will be subjected to stripping so as to produce a stripped solution and gaseous carbon dioxide and ammonia. The gaseous components will be condensed in the condenser, resulting in ammonium carbamate that is recirculated to the reactor. Depending on the type of condenser, a considerable amount of conversion of ammonium carbamate into urea may also occur in the condenser. Also, the condenser and the reactor can be integrated into a single apparatus.

In the process of the invention, the stripped solution is subjected to further separation so as to obtain an aqueous urea stream, and a gas stream comprising $CO_2$ and $NH_3$. This separation generally takes place at a pressure lower than that in the synthesis section. Such lower pressure can be medium pressure (MP), low pressure (LP), or can involve both. MP and LP recirculation sections (also referred to as recovery sections) are well-known to the skilled person. The prevailing pressures are generally of the order of 1-10 MPa, more typically 1-5 MPa for a MP section and 0.1 to 1 MPa, more typically 0.2 to 0.6 MPa, for a LP section. The plant of the invention and the plant modification methods of the invention are configured to accommodate conducting the process as described, by providing the appropriate MP and/or LP recirculation sections.

A frequently used urea stripping process is the carbon dioxide stripping process as for example described in Ullmann's Encyclopedia of Industrial Chemistry, Vol. A27, 1996, pp 333-350. In this process, the synthesis section is followed by one or more recovery sections. The synthesis section comprises a reactor, a stripper, a condenser and a scrubber in which the operating pressure is in between 12 and 18 MPa and preferably in between 13 and 16 MPa. In the synthesis section the urea solution leaving the urea reactor is fed to a stripper in which a large amount of non-converted ammonia and carbon dioxide is separated from the aqueous urea solution. Such a stripper can be a shell and tube heat exchanger in which the urea solution is fed to the top part at the tube side and a carbon dioxide feed to the synthesis is added to the bottom part of the stripper. At the shell side, steam is added to heat the solution. The urea solution leaves the heat exchanger at the bottom part, while the vapor phase leaves the stripper at the top part. The vapor leaving said stripper contains ammonia, carbon dioxide and a small amount of water. Said vapor is condensed in a falling film type heat exchanger or a submerged type of condenser that can be a horizontal type or a vertical type. A horizontal type submerged heat exchanger is described in Ullmann's Encyclopedia of Industrial Chemistry, Vol. A27, 1996, pp 333-350. The heat released by the exothermic carbamate condensation reaction in said condenser is usually used to produce steam that is used in a downstream urea processing section for heating and concentrating the urea solution. Since a certain liquid residence time is created in a submerged type condenser, a part of the urea reaction takes already place in said condenser. The formed solution, containing condensed ammonia, carbon dioxide, water and urea together with the non-condensed ammonia, carbon dioxide and inert vapor is sent to the reactor. In the reactor the above mentioned reaction from carbamate to urea approaches the equilibrium. The ammonia to carbon dioxide molar ratio in the urea solution leaving the reactor is generally in between 2.5 and 4 mol/mol. It is also possible that the condenser and the reactor are combined in one piece of equipment. An example of this piece of equipment as described in Ullmann's Encyclopedia of Industrial Chemistry, Vol. A27, 1996, pp 333-350. The formed urea solution leaving the urea reactor is supplied to the stripper and the inert vapor containing non-condensed ammonia and carbon dioxide is sent to a scrubbing section operating at a similar pressure as the reactor, or said vapor is sent directly to the ammonium nitrate section for neutralization (i.e. reaction with nitric acid so as to form ammonium nitrate). In that scrubbing section the ammonia and carbon dioxide is scrubbed from the inert vapor. The formed carbamate solution from the downstream recovery system is used as absorbent in that scrubbing section. The urea solution leaving the stripper in this synthesis section requires a urea concentration of at least 45% by weight and preferably at least 50% by weight to be treated in one single recovery system downstream the stripper. The recovery section comprises a heater, a liquid/gas separator and a condenser. The pressure in this recovery section is between 200 to 600 kPa. In the heater of the recovery section the bulk of ammonia and carbon dioxide is separated from the urea and water phase by heating the urea solution. Usually steam is used as heating agent. The urea and water phase, contains a small amount of dissolved ammonia and carbon dioxide that leaves the recovery section and is sent to a downstream urea processing section where the urea solution is concentrated by evaporating the water from said solution.

The invention is not limited to any particular urea production process. Other processes and plants include those that are based on technology such as total recycle plants, the HEC process developed by Urea Casale, the ACES process developed by Toyo Engineering Corporation and the process developed by Snamprogetti. All of these processes, and others, may be used in the method of the invention.

In one embodiment, the urea purification section comprises a rectification column containing a shell and tube heat exchanger and a gas/liquid separator wherein the aqueous urea solution is flowing through the tubes and steam is used on the shell side. In another embodiment a strip gas may also be used.

The purpose of the purification section is to remove $CO_2$ and ammonia from the aqueous urea solution produced in the synthesis section. The aqueous urea solution generally comprises urea, ammonium carbamate and unreacted $CO_2$ and $NH_3$. As is well known to the skilled person, $CO_2$ and $NH_3$ in an aqueous urea solution are in equilibrium with ammonium carbamate. The formation of ammonium carbamate from $CO_2$ and ammonia is an exothermic reaction. The removal of $CO_2$ and ammonia from the aqueous solution may be effected by the addition of heat and/or the reduction of pressure optionally with the use of a stripping agent. The transition of $CO_2$ and ammonia into the gas phase (evaporation) will shift the equilibrium of ammonium carbamate thereby promoting the dissociation of ammonium carbamate which in turn promotes the evaporation of $CO_2$ and ammonia.

In a urea plant, the equipment used for the purification step is generally named by the major function it is assigned to do. The terms carbamate recovery system, dissociator, stripper, (pre-)evaporator are commonly used. The purification step may be carried out in the same type of equipment as is used in the recovery section of a standard urea plant. For example a rectifying column may be used. Alternatively a shell and tube heat exchanger may be used with optionally a gas/liquid separator in the top of the vessel, or a separate gas/liquid separator. The purification step may be carried out in one or more steps. Other configurations and equipment are known to the skilled person. As an optional stripping agent CO2, ammonia or steam may be used. In a standard recovery section the raw materials ammonia and CO2 are recycled back to the urea synthesis section, therefore it is undesirable to use steam as a stripping agent as this would lead to an increase in the recycle of water to the urea synthesis section. The invention allows avoiding this limitation. In the event that, as preferred, no ammonia is recycled to the synthesis section, the presence of water after the purification section is not an issue.

Part of the aqueous urea stream obtained from the purification section of a urea plant, is used in making DEF. The DEF production unit applies for example (thermal) stripping with pressurized steam based on direct injection (FIG. 3) or evaporation in a heat exchanger with pressurized steam by means of a shell and tube or plate heat exchanger (FIG. 4) for product quality control on ammonia content at the outlet of the urea synthesis section. Such stripping is applied to remove excessive ammonia to comply with the DEF final product specification of 0.2 wt % ammonia.

Figure 3:
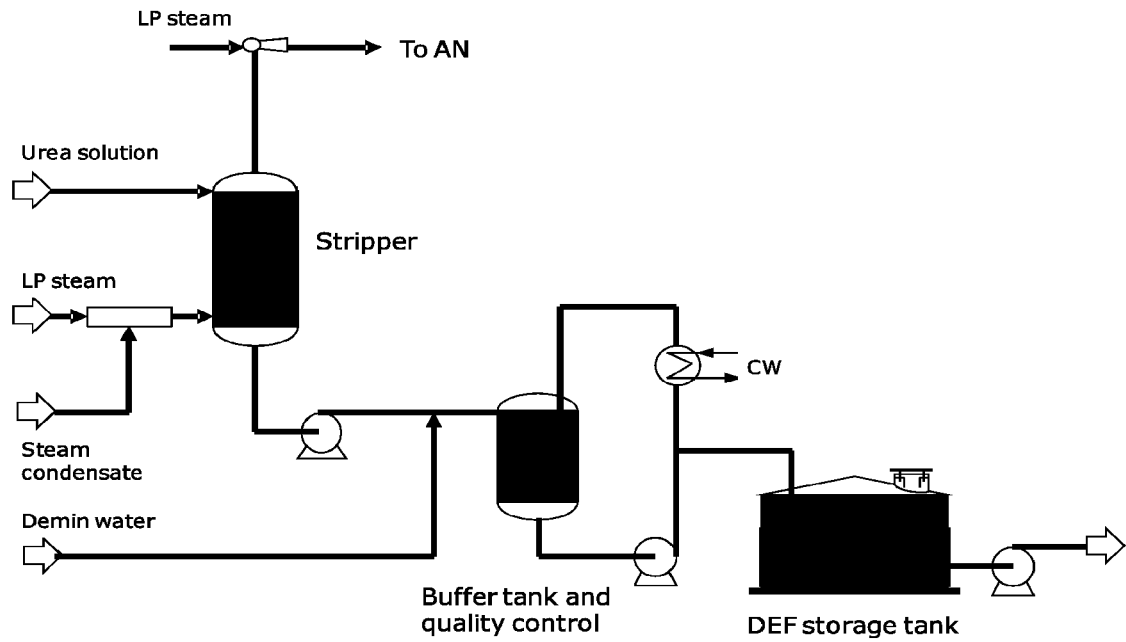
Figure 5:
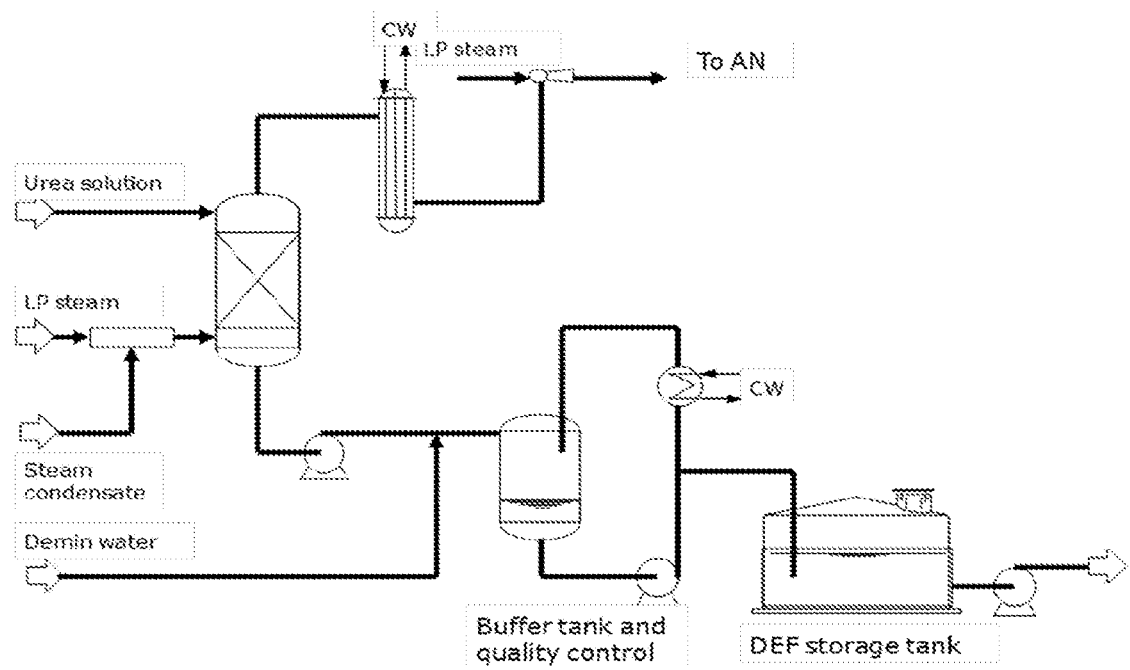

If necessary the off-gasses from the thermal stripper are condensed and boosted with a steam ejector in at least one stage and to be combined with the regular synthesis off-gasses send to the neutralizer in the ammonia nitrate section. Alternatively, these off gases are sent directly to the neutralizer (or after neutralizer) section in the ammonia nitrate production unit (FIGS. 3 and 5). The released ammonia is thereby used to neutralize the nitric acid in order to produce ammonium nitrate. In this way the regular ammonia used for neutralization can be reduced by using the ammonia from the thermal stripper, reducing the virgin ammonia consumption of the ammonia nitrate plant. This arrangement can be applied with any urea synthesis arrangement. This method facilitates an efficient small dedicated DEF production or it can be aligned for large scale DEF production similar to the capacity of the urea synthesis.

An alternative to the aforementioned stripping is to optimize the urea melt concentration at the stage of urea synthesis. In the case of ammonia or carbon dioxide stripping the following variables are applied to obtain a urea melt solution suitable for DEF production:

Higher stripping efficiency in the HP stripper (0.70-0.95)
Higher pressure in the low pressure section (4-8 bar)
Higher pressure in the medium pressure recovery section (15-40 bar)
Higher temperature applied by the low pressure rectifying heater (90-145° C.)
Increase of the condensation or reactor efficiency.

The invention can also be put to use in a method for the modernization of a pre-existing urea plant. Such a plant comprises a urea synthesis section and, downstream thereof and in fluid communication therewith, a urea purification section suitable for separating off CO2 and NH3 from an aqueous urea solution comprising said CO2 and NH3. The method comprising adding to the urea plant a unit for the production of ammonium nitrate from ammonia and nitric acid. Thereby an outlet for NH3 from the purification section of the urea plant is to be connected to an inlet for NH3 of the unit for the production of ammonium nitrate. Also, an outlet for an aqueous urea solution from the purification section and an outlet for an aqueous ammonium nitrate solution from the unit for the production of ammonium nitrate, are connected to a unit for mixing said aqueous urea solution and said aqueous ammonium nitrate solution.

An advantage of the modernized plant is that it provides an additional possibility for using ammonia retrieved from the urea plant, allowing waste water treatment to be dispensed with.

It will be understood that the invention also pertains to building new urea plants, integrated with a production unit for ammonium nitrate. A great advantage, as discussed above, is that the new plant can be built without an evaporation section and a wastewater treatment section. It is noted that one can also build the new plant with these sections, if a greater versatility of different urea products (including solid urea forms, such as prills or granules) is desired in addition to DEF and UAN. Also, with the view to producing powder that can be diluted DEF as discussed above, a new urea production unit in an integrated system of the invention be built with a (flash) crystallization section, but—if desired—without a shaping section as would traditionally have been applied to produce solid urea forms such as prills or granules.

The invention is further illustrated with reference to the drawings. It will be understood that the drawings are not limiting the invention. E.g., the invention is not limited to the specific types of equipment and specific plant systems as shown. All figures show schematic drawings of equipment parts and process streams relating to embodiments of the invention. Components and streams are indicated in the drawings by short keywords.

In FIG. 1 NH3 and CO2 are fed to a urea synthesis zone. Shown is an embodiment in which NH3 is fed to the a urea synthesis reactor, and CO2 is fed to a high pressure stripper. The urea synthesis solution formed is led to a purification section. Therein non-reacted NH3 and CO2 are removed from the synthesis solution. Part of the resulting aqueous urea stream is used to obtain DEF, and part is used to be mixed with ammonium nitrate (not shown) so as to obtain UAN. The removed NH3, rather than being recirculated to urea synthesis, is sent to a unit (not shown) for the production of ammonium nitrate.

It is noted that it also conceivable to use a part of the NH3 for the production of ammonium nitrate, and recycle another part to urea synthesis. It is preferred, however, to make full use of the benefits of the invention by not recycling any of the ammonia.

Figure 2:
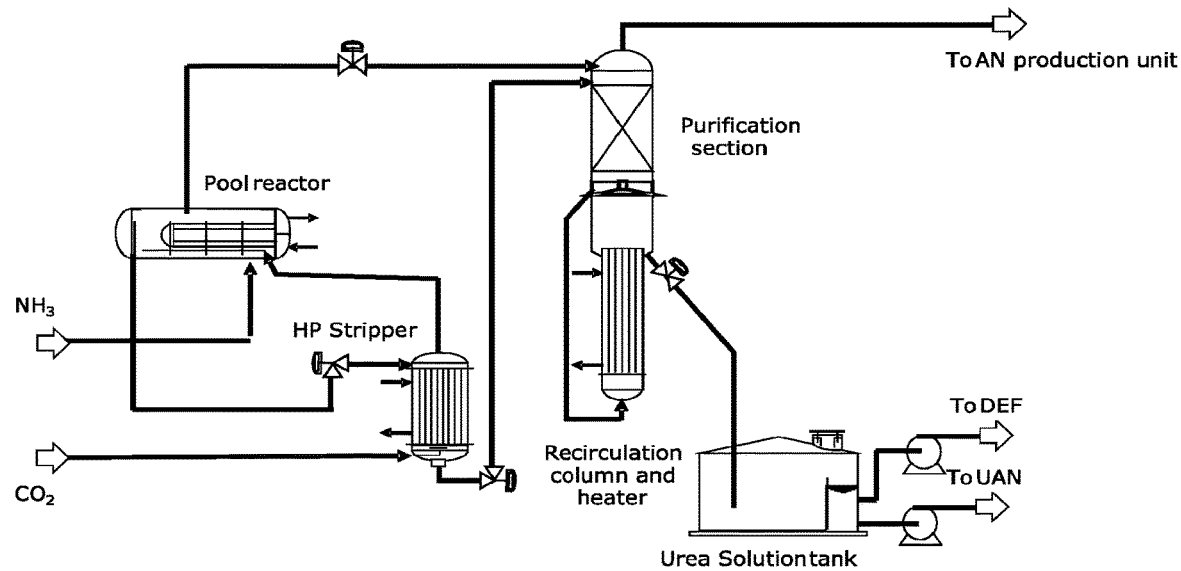

FIG. 2 is similar to FIG. 1. Here the aqueous urea solution is sent to a tank. Therefrom the process choice can be made to use the aqueous urea in the production of UAN, in the production of DEF, or in both. This has the advantage of providing a buffer amount of the aqueous urea solution, which adds to the flexibility of the process.

FIG. 3 shows DEF production by means of steam stripping with direct steam injection, and with off-gas sent to a unit for the production of ammonium nitrate, via LP steam injection.

Figure 4:
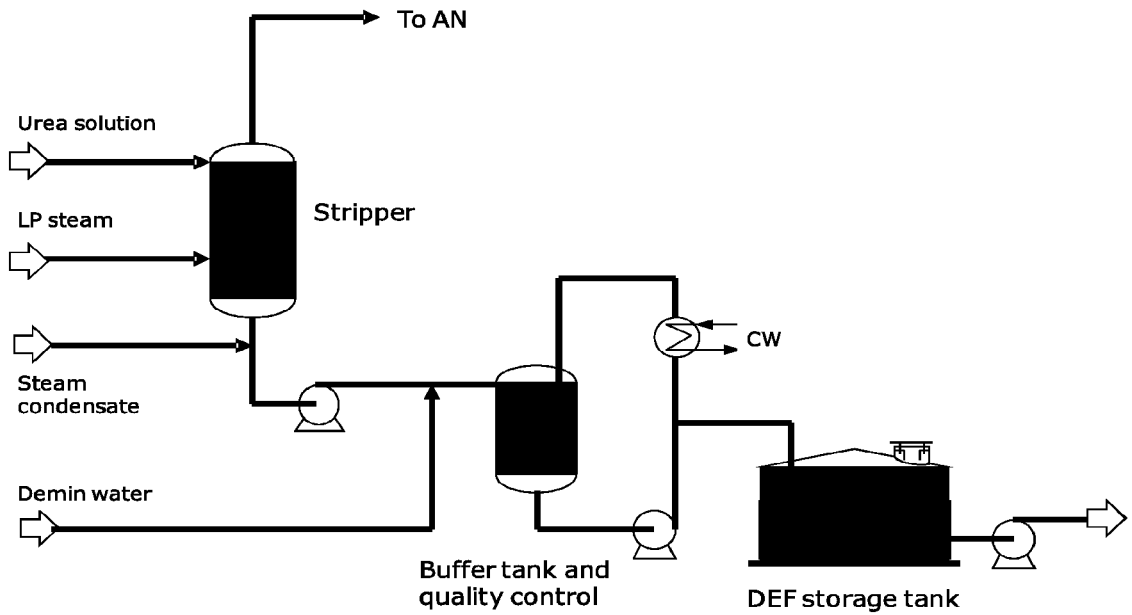

FIG. 4 shows DEF production with a thermal stripper. In accordance with the integrated production of DEF and UAN of the invention, off-gas from the thermal stripper is sent to the AN neutralizer, rather than to a gas treatment and waste water section for cleaning.

FIG. 5 shows a configuration similar to that of FIG. 4, whereby use is made of a condenser and steam injector, as an alternative route to send the off-gasses to the AN section for neutralization. While the invention has been illustrated and described in detail in the drawings and foregoing description, such illustration and description are to be considered illustrative or exemplary and not restrictive; the invention is not limited to the disclosed embodiments.

For example, it is possible to operate the invention in an embodiment wherein more than one aqueous stream is separated from different places in or after the recovery section, to obtain the aqueous urea solution.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain features of the invention are recited in mutually different dependent claims does not indicate that a combination of these features cannot be used to advantage.

In sum, the invention includes a method for the integrated production of two different urea products. One is an aqueous urea solution suitable for use in NOx abatement (generally indicated as Diesel Exhaust Fluid—DEF). The other is a solution used as a fertilizer, viz. Urea Ammonium Nitrate (UAN). The production of DEF and UAN are integrated as follows: ammonia recovered from the production of urea is used as a feed to the production of ammonium nitrate. At least part of an aqueous urea stream from urea production, is mixed with ammonium nitrate so as to obtain UAN.

The invention claimed is:

1. A method for modernizing a urea plant for the integrated production of urea and urea ammonium nitrate, the plant comprising a urea synthesis section and urea purification section downstream of said synthesis section and in fluid communication with said synthesis section, wherein said synthesis section comprises a reactor, a stripper and a condenser in fluid communication with each other so as to form a urea synthesis loop, wherein said urea purification section is configured to separate off $CO_2$ and $NH_3$ form an aqueous urea solution comprising said $CO_2$ and $NH_3$, thereby giving purified aqueous urea solution, wherein said purification section has an outlet for said purified aqueous urea solution and an outlet for $NH_3$, the method comprising adding to the urea plant a unit for the production of aqueous ammonium nitrate solution from ammonia and nitric acid, such that the outlet for $NH_3$ from the purification section of the urea plant is connected to an inlet for $NH_3$ of the unit for the production of aqueous ammonium nitrate solution and said outlet for purified aqueous urea solution from the purification section is connected to a first purified aqueous urea solution outlet and a second purified aqueous urea solution outlet and said first purified aqueous urea solution outlet is connected to a unit for mixing said aqueous ammonium nitrate solution and said purified aqueous urea solution, and an outlet for said aqueous ammonium nitrate solution from the unit for the production of aqueous ammonium nitrate solution is connected to said unit for mixing, and wherein the method further comprises adding to the urea plant a Diesel Exhaust Fluid production unit having an inlet for said purified aqueous urea solution such that said Diesel Exhaust Fluid production unit inlet is connect with said second purified aqueous urea solution outlet, the Diesel Exhaust Fluid production unit further comprising (a) an inlet for demineralized water, such that a diluting section is configured for diluting said purified aqueous urea solution or part thereof with said demineralized water, or (b) a flash crystallization unit configured for flash crystallization of said purified aqueous urea solution or part thereof to form a solid urea powder, the method further comprising providing the Diesel Exhaust Fluid production unit with a Diesel Exhaust Fluid production stripper having an inlet for pressurized steam, and outlet for an off-gas, and an inlet for said purified aqueous urea solution such that said Diesel Exhaust Fluid production stripper is configured for stripping of said purified aqueous urea solution from said second outlet with direct injection of pressurized steam, and further comprising providing a connection from said outlet for off-gas of said Diesel Exhaust Fluid production stripper to said unit for the production of aqueous ammonium nitrate solution.

2. The method according to claim 1 further comprising connecting a urea solution tank between the purification section outlet for said purified aqueous urea solution and the first and second outlets for the purified aqueous urea solution.

3. A method for modernizing a plant for the production of ammonium nitrate for the integrated production of urea and urea ammonium nitrate, said plant comprising a unit for the synthesis of ammonium nitrate from ammonia and nitric acid, the method comprising adding to the plant for the production of ammonium nitrate a plant for the production of urea, wherein the plant for the production of urea comprises a urea synthesis section comprising a reactor, a stripper and a condenser in fluid communication with each other so as to form a urea synthesis loop and downstream of the synthesis section and in fluid communication therewith, a urea purification section suitable for separating off $CO_2$ and $NH_3$ from an aqueous urea solution comprising said $CO_2$ and $NH_3$ to form a purified aqueous urea solution, such that an outlet for $NH_3$ from the purification section of the urea plant is connected to an inlet for $NH_3$ of the unit for the production of ammonium nitrate, such that the purification section comprises an outlet for the purified aqueous urea solution that is connected to a first outlet for the purified aqueous urea solution and a second outlet for the purified aqueous urea solution, and said first outlet for the purified aqueous urea solution and an outlet for an aqueous ammonium nitrate solution from the unit for the production of ammonium nitrate are connected to a unit for mixing said aqueous urea solution and said aqueous ammonium nitrate solution, and wherein the method further comprises adding to the plant for the production of ammonium nitrate a Diesel Exhaust Fluid production unit having an inlet for said purified aqueous urea solution such that said Diesel Exhaust Fluid production unit inlet is connected with said second purified aqueous urea solution outlet, the Diesel Exhaust Fluid production unit further comprising (a) an inlet for demineralized water, such that a diluting section is configured for diluting said purified aqueous urea solution or part thereof with said demineralized water, or (b) a flash crystallization unit configured for flash crystallization of said purified aqueous urea solution or part thereof to form a solid urea powder, the method further comprising providing the Diesel Exhaust Fluid production unit with a Diesel Exhaust Fluid production stripper having an inlet for pressurized steam, an outlet for an off-gas, and an inlet for said purified aqueous urea solution such that said Diesel Exhaust Fluid production stripper is configured for stripping of said purified aqueous urea solution from said second outlet with direct injection of pressurized steam, and further comprising providing a connection from said outlet for off-gas of said Diesel Exhaust Fluid production stripper to said unit for the production of aqueous ammonium nitrate solution.

4. The method according to claim 3 further comprising connecting a urea solution tank between the purification section outlet for the purified aqueous urea solution and the first and second outlets for the purified aqueous urea solution.

* * * * *